United States Patent
Nonaka et al.

(10) Patent No.: US 9,624,279 B2
(45) Date of Patent: Apr. 18, 2017

(54) METHOD FOR PRODUCING INSOLUBLE AGGREGATE OF NEURODEGENERATIVE-DISEASE-RELATED PROTEIN

(75) Inventors: Takashi Nonaka, Tokyo (JP); Masami Masuda, Tokyo (JP); Makiko Yamashita, Tokyo (JP); Haruhiko Akiyama, Tokyo (JP); Masato Hasegawa, Tokyo (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 156 days.

(21) Appl. No.: 14/348,024

(22) PCT Filed: May 18, 2012

(86) PCT No.: PCT/JP2012/062794
§ 371 (c)(1),
(2), (4) Date: Mar. 27, 2014

(87) PCT Pub. No.: WO2013/073219
PCT Pub. Date: May 23, 2013

(65) Prior Publication Data
US 2014/0248657 A1 Sep. 4, 2014

(30) Foreign Application Priority Data
Nov. 18, 2011 (JP) ................................. 2011-252522

(51) Int. Cl.
*C07K 14/47* (2006.01)
*C12P 21/02* (2006.01)
*G01N 33/68* (2006.01)
*G01N 33/50* (2006.01)

(52) U.S. Cl.
CPC .......... *C07K 14/47* (2013.01); *C07K 14/4711* (2013.01); *C12P 21/02* (2013.01); *G01N 33/5058* (2013.01); *G01N 33/6896* (2013.01)

(58) Field of Classification Search
None
See application file for complete search history.

(56) References Cited

U.S. PATENT DOCUMENTS

2010/0047826 A1  2/2010  Nonaka et al.

FOREIGN PATENT DOCUMENTS

| EP | 2 272 955 A1 | 1/2011 |
|----|--------------|--------|
| WO | WO 2007/066809 A1 | 6/2007 |
| WO | WO 2009/008529 A1 | 1/2009 |
| WO | WO 2009/125646 A1 | 10/2009 |

OTHER PUBLICATIONS

Kimura, T. et al. 2010. Aggregation of detergent-insoluble Tau is involved in neuronal loss but not synaptic loss. Journal of Biological Chemistry 285(49): 38692-38699. specif. pp. 38692, 38693, 38696.*

Tandon, A. et al. 2003. Brain levels of CDK5 activator p25 are not increased in Alzheimer's or other neurodegenerative diseases with neurofibrillary tangles. Journal of Neurochemistry 86: 572-581. specif. p. 573.*

Luk, K.C. et al. 2009. Exogenous a-synuclein fibrils seed the formation of Lewy body-like intracellular inclusions in cultured cells. Proceedings of the National Academy of Science (PNAS) 106(47): 20051-20056. specif. pp. 20051, 20052, 20053, 20056.*

Nonaka, T. et al. 2009. Truncation and pathogenic mutations facilitate the formation of intracellular aggregates of TDP-43. Human Molecular Genetics 18(18): 3353-3364. specif. pp. 3353, 3354.*

Nishimoto, Y. et al. Jan. 1, 2010. Characterization of alternative isoforms and inclusion body of the TAR DNA-binding protein-43. Journal of Biological Chemistry 285(1): 608-619. specif. pp.*

Clontech. pAcGFP-C1. Datasheet [online]. Clontech Laboratories, Inc., 2004 [retrieved on Jul. 17, 2016]. Retrieved from the Internet: <URL:http://www.clontech.com/US/Products/Fluorescent_Proteins_and_Reporters/Fluorescent_Proteins_by_Name/ibcGetAttachment.jsp?cItemId=17846&fileId=5878131&sitex=10020:22372:US> pp. 1-2.*

Qin, J.Y. et al. May 2010. Systematic comparison of constitutive promoters and the doxycycline-inducible promoter. PLoS One 5(5):1-4.specif. p. 1.*

Danzer, K.M. et al. "Seeding induced by α-synuclein oligomers provides evidence for spreading of α-synuclein pathology," Journal of Neurochemistry, 2009, vol. 111, No. 1, pp. 192-203.

International Search Report issued in PCT/JP2012/062794 mailed Aug. 21, 2012.

Nonaka, T. et al. "Seeded Aggregation and Toxicity of α-Synuclein and Tau Cellular Models of Neurodegenerative Diseases," Journal of Biological Chemistry, 2010, vol. 285, No. 45, pp. 34885-34898.

Chinese Office Action issued in Chinese Patent Application No. 2012800440015 on Sep. 7, 2015, with English translation.

Colby et al., Prion Detection by an Amyloid Seeding Assay, PNAS, Dec. 26, 2007, vol. 104, No. 52, pp. 20914-20919.

Extended European Search Report issued in European Patent Application No. 12848991.1 on Oct. 9, 2015.

(Continued)

*Primary Examiner* — Renee Claytor
*Assistant Examiner* — Sharon M Papciak
(74) *Attorney, Agent, or Firm* — Birch, Stewart, Kolasch & Birch, LLP

(57) ABSTRACT

The purpose of the present invention is to develop a method for amplifying in vitro to a large amount of a homogenous insoluble aggregate that is equivalent to an insoluble aggregate formed in the brain of a patient. A method of producing an insoluble aggregate including TDP-43 protein and fragments thereof according to the present invention includes the steps of: (1) introducing an insoluble fraction originated from the brain of a neurodegenerative disease patient into a cell culture in which the intact TDP-43 protein can be expressed in a constitutive manner; (2) culturing the cultured cell into which the insoluble fraction has been introduced; and (3) separating an insoluble fraction from the cultured cell. Optionally, the method may additionally include a step of amplifying the insoluble aggregate of the neurodegenerative-disease-related protein in the cultured cell.

9 Claims, 12 Drawing Sheets

(56) References Cited

OTHER PUBLICATIONS

Furukawa et al., "A Seeding Reaction Recapitulates Intracellular Formation of Sarkosyl-insoluble Transactivation Response Elemetn (TAR) DNA-binding Protein-43 Inclusions", Journal of Biological Chemistry, May 27, 2011, vol. 286, No. 21, pp. 18664-18672.
Liu-Yesucevitz, "Tar DNA Binding Protein-43 (TDP-43) Associates with Stress Granules: Analysis of Cultured Cells and Pathological Brain Tissue", PLOS One, vol. 5, No. 10 (2010) pp. 1-15.
Nonaka et al., "Prion-like Properties of Pathological TDP-43 Aggregates from Diseased Brains", Cell Reports, vol. 4 (2013) pp. 124-134.
Nonaka et al., "In vitro recapitulation of aberrant protein inclusions in neurodegenerative diseases," Communicative and Integrative Biology, vol. 4, No. 4, Jul./Aug. 2011, pp. 501-502.
Nonaka et al., "Phosphorylated and ubiquitinated TDP-43 pathological inclusions in ALS and FTLD-U are recapitulated in SH-SY5Y cells," FEBS Letters, vol. 583, No. 2, 2009, pp. 394-400.

\* cited by examiner

METHOD FOR PRODUCING INSOLUBLE AGGREGATE OF NEURODEGENERATIVE-DISEASE-RELATED PROTEIN

TECHNICAL FIELD

The present invention relates to a method of producing an insoluble aggregate of human neurodegenerative-disease-related protein and an insoluble aggregate produced by the method, particularly a method of producing an insoluble aggregate and an insoluble aggregate produced by the method that is performed by repeating a step of forming an insoluble aggregate using an insoluble fraction originated from the brain of a neurodegenerative disease patient as a seed in a cultured cell expressing a neurodegenerative-disease-related protein in a constitutive manner.

BACKGROUND ART

As for most neurodegenerative diseases, an intracellular inclusion (aggregate) unique to each disease is found in the brain of the neurodegenerative disease patient. Both neurofibrillary tangle observed in Alzheimer's disease (AD) and a pathological construct designated as "Lewy bodies" in Parkinson's disease (PD), are insoluble aggregates consisting of various kinds of proteins. Tau has been identified as the major component of neurofibrillary tangle; so have been α-synuclein as the major component of Lewy bodies; and TAR DNA-binding protein 43 kDa (TDP-43) as the major component of ubiquitin positive-intracellular inclusion that is observed in amyotrophic lateral sclerosis (ALS), respectively. While these proteins are present as soluble proteins in a normal subject, they are accumulated as insoluble and abnormal aggregates in the brain of a patient, the mechanism of which having remained unclear so far. Also, since correlations are observed between the sites where the aggregates appear and the sites of neuronal deficit (cell death), there is considered a mechanism that the aggregates appearing in the cell have cytotoxicity such that the deaths of neuronal cells eventually take place and that the onset of the diseases is thereby triggered. Accordingly, it is considered that elucidation of, for example, the mechanism of intracellular inclusion formation and the mechanism of induction of cell death by aggregates may contribute to the development of therapeutic agents for various neurodegenerative diseases.

For the purpose of the development of therapeutic agents, it is necessary to construct a system which can mimic the formation of distinctive intracellular inclusion of each disease in cultured cells. However, by simply expressing proteins for forming the aggregates in the cells, no aggregates observed in the brains of patients can be formed at all. In recent years, the inventors of the present application have established a method to efficiently introduce the protein aggregates prepared in vitro into cultured cells (patent document 1 and non-patent document 1). The inventors in the present application found that aggregates having a property and configuration similar to the intracellular inclusions observed in the brains of patients could be formed as a result of introducing the aggregates prepared in vitro into the cells in which the protein had been transiently expressed in advance. The formation of the aggregates is not observed at all when proteins of aggregates are merely transiently expressed in the cells. However, new aggregates are formed when the aggregates of the proteins prepared in vitro are introduced into the cells and then act as a nucleus i.e. seed of the aggregation.

PRIOR ART DOCUMENTS

Patent Document

Patent document 1: International Publication No. WO2007/066809

Non-Patent Document

Non-patent document 1: Nonaka, T. et al., J. Biol. Chem. 285:34885 (2010)

SUMMARY OF THE INVENTION

Problem to be Solved by the Invention

The aggregates formed in the cells based on the protein aggregates prepared in vitro are different from the insoluble aggregates which appear in association with the progression of neurodegenerative diseases in effect. Thus, for the purpose of replicating the processes of developing the neurodegenerative diseases, it is needed to develop an experimental system which mimics the processes of forming the aggregates in the cell where the insoluble aggregates formed in the brain of neurodegenerative diseases work as a seed. And also, a large amount of the insoluble aggregates formed in the brains of patients are needed to be obtained for analyzing the process for forming the aggregates in the cell in detail. However, since the amount of the insoluble aggregates formed in the brains of patients is limited, it is needed to develop a method of producing a homogeneous insoluble aggregate.

Means to Solve the Problem

The present invention provides a method of producing an insoluble aggregate of neurodegenerative-disease-related protein. The method of producing an insoluble aggregate of neurodegenerative-disease-related protein in the present invention comprises (1) a step of introducing an insoluble fraction originated from the brain of a neurodegenerative disease patient into a culture cell expressing the neurodegenerative-disease-related protein in a constitutive manner, (2) a step of incubating the culture cell with the insoluble fraction already introduced thereinto, and (3) a step of separating an insoluble fraction from the incubated culture cell.

The method of producing the insoluble aggregate of neurodegenerative-disease-related protein in the present invention may comprise (4) a step of amplifying the insoluble aggregate of neurodegenerative-disease-related protein in a cultured cell, comprising introducing the insoluble fraction separated from the culture cell into the cultured cell expressing the neurodegenerative-disease-related protein in a constitutive manner, followed by incubating the cultured cell introduced the insoluble fraction, then separating an insoluble fraction from the cultured cell.

The method of producing an insoluble aggregate of a neurodegenerative-disease-related protein in the present invention may comprise (5) a step of further repeating the step of (4) in succession at least one time.

In the method of producing an insoluble aggregate of a neurodegenerative-disease-related protein in the present invention, the neurodegenerative-disease-related protein may be selected from the group consisting of TAR DNA binding protein, α-synuclein, Tau protein, β-amyloid protein, polyglutamine, SOD 1 and a prion protein.

The present invention provides an insoluble aggregate of a neurodegenerative-disease-related protein obtained by the method in the present invention.

The present invention provides a method of producing an insoluble aggregate of a neurodegenerative-disease-related protein from a biological sample. The method of producing an insoluble aggregate of a neurodegenerative-disease-related protein from the biological sample may comprise (1) a step of introducing an insoluble fraction separated from the biological sample into a cultured cell expressing the neurodegenerative-disease-related protein in a constitutive manner, (2) a step of incubating the culture cell with the insoluble fraction already introduced thereinto, and (3) a step of separating an insoluble fraction from the incubated culture cell.

The method of producing an insoluble aggregate of a neurodegenerative-disease-related protein from the biological sample in the present invention may comprise (4) a step of amplifying the insoluble aggregate of neurodegenerative-disease-related protein in the cultured cell, comprising introducing the insoluble fraction separated from the culture cell into the cultured cell expressing the neurodegenerative-disease-related protein in a constitutive manner, followed by incubating the cultured cell introduced, and separating an insoluble fraction from the cultured cell.

The method of producing the insoluble aggregate of neurodegenerative-disease-related protein from the biological sample in the present invention may comprise (5) a step of further repeating the step of (4) in succession at least one time.

The present invention provides the insoluble aggregate of neurodegenerative-disease-related protein from the biological sample obtained by the method in the present invention.

The present invention provides a method of examining cytotoxicity in a biological sample. The method of examining the cytotoxicity in the biological sample in the present invention may comprise a step of introducing an insoluble fraction of the neurodegenerative-disease-related protein in the present invention or an insoluble fraction originated from the brain of a neurodegenerative disease patient into a cultured cell expressing the neurodegenerative-disease-related protein in a constitutive manner, and a step of quantifying a degree of cell death of the cultured cell.

The present invention provides a method of screening a therapeutic agent for a neurodegenerative disease. The method of screening a therapeutic agent for a neurodegenerative disease comprises a step of introducing the insoluble fraction of the neurodegenerative-disease-related protein in the present invention or the insoluble fraction originated from the brain of a neurodegenerative disease patient into a cultured cell expressing the neurodegenerative-disease-related protein in a constitutive manner, a step of bringing the therapeutic agent candidate into contact with the neurodegenerative disease to the cultured cell, and a step of screening a candidate compound having a suppressing effect on a cell death of the cultured cell as a therapeutic agent candidate for the neurodegenerative disease.

In this specification, a "neurodegenerative disease" refers to a disease having distinctive pathological structures present in the neurons of the brains of patients, i.e. insoluble aggregates (amyloid fibrils) composed of various proteins, wherein Alzheimer's disease (AD), Parkinson's disease (PD), amyotrophic lateral sclerosis (ALS), frontotemporal lobar degeneration (FTLD), progressive supranuclear palsy (PSP), corticobasal degeneration (CBD), Pick's disease (Pick) and the like are known as the disease. It is considered that the insoluble aggregates cause cytotoxicity, finally neuronal cell death and pathogenesis.

In this specification, a "neurodegenerative-disease-related protein" refers to proteins of major component in the insoluble aggregates which present in neurodegenerative disease, wherein Tau which is one of microtubule associated proteins in Alzheimer's disease, α-synuclein in Parkinson's disease and TAR DNA-binding protein 43 kDa (TDP-43) in amyotrophic lateral sclerosis and frontotemporal lobar degeneration are identified as the neurodegenerative-disease-related proteins, respectively. Tau is a protein of molecular weight 55 to 62 kDa and its six isoforms are present by selective splicing. The isoforms are classified into the 4-repeat Tau having four microtubule associated sites and the 3-repeat Tau having three microtubule associated sites. The neurodegenerative disease associated with Tau accumulation is collectively called as tauopathy, and it is known that Tau isoforms in accumulation are different in each disease. All six isoforms accumulate in paired helical filament (PHF) of AD, while the aggregates which 4-repeat Tau mainly accumulates are observed in progressive supranuclear palsy (PSP), corticobasal degeneration (CBD) and the like. And also, the distinctive aggregates which 3-repeat Tau mainly accumulates appear in Pick's disease. In addition to the 4-repeat Tau and the 3-repeat Tau, the neurodegenerative-disease-related proteins in this specification include β-amyloid protein, polyglutamine, SOD 1 and a prion protein.

In the present invention, a "culture cell expressing a neurodegenerative-disease-related protein in a constitutive manner" may be any type of cell, provided that an insoluble aggregate can be formed in each disease. The culture cell expressing the neurodegenerative-disease-related protein in a constitutive manner is preferably a cell having properties similar to a neuron. The origin may be a cell derived from a neurodegenerative disease patient or a cell obtained independently of the disease. The origin of the culture cell expressing the neurodegenerative-disease-related protein in a constitutive manner may be a cell belonging to a cell lineage of a neuron or a tumor cell originated from a cell lineage of a neuron. The neuroblastoma cell lines include, but are not limited to: KELLY, SH-SY5Y, SK-N-AS, SK-N-F1, SK-N-DZ, BE(2)-C, BE(2)-M17, SK-N-BE(2) and SK-N-SH, and these cell lines may be used as the culture cell expressing the neurodegenerative-disease-related protein in a constitutive manner. The culture cell expressing the neurodegenerative-disease-related protein may be the origin of a neuron differentiated from iPS cell, ES cell, mesenchymal stem cell and the other multipotential stem cell. Alternatively, the origin may be a neuron differentiated from the other cell type except neuron by direct transdifferentiation.

In the present invention, the term "expressing the neurodegenerative-disease-related protein in a constitutive manner" indicates expressing any of the neurodegenerative-disease-related proteins-expressed transiently or stably the neurodegenerative-disease-related proteins may be expressed by any procedures, provided that the neurodegenerative-disease-related proteins have been expressed in several cells in the introduction of insoluble fraction. In the introduction, the procedures include, but are not limited to: electroporation, calcium phosphate method, viral vector method and the like. It is preferable that lipofection method exerts less injury to the cell in the introduction of exogenous DNA. Any reagents known to a person skilled in the art may be used as the reagents used in the procedures. The X-tremeGENE 9 used in this specification in addition to commercially available reagents, i.e. FuGENE 6, Lipofectin, Lipofectamine, MultiFectam and the like may be used.

In the specification, the term "insoluble fraction" refers to a fraction which is not solved in a solution comprising a detergent. In the specification, an insoluble fraction refers to a fraction which cannot be solved with sarkosyl and can be precipitated by centrifugation. The insoluble fraction may be originated from the brain tissues of neurodegenerative disease patients or the cultured cells. The insoluble fractions in the present invention may be the insoluble fractions originated from the brains; the insoluble fraction separated from the cultured cells which introduced the insoluble fractions originated from the brains and incubated for a few days; the insoluble fractions separated from the cultured cells which introduced the insoluble fractions originated from the cultured cells and incubated for a few days; and the insoluble fractions obtained by one or more repetitions of introductions and separations of the insoluble fractions.

In the present invention, a step of introducing an insoluble fraction into the culture cell expressing the neurodegenerative-disease-related protein in a constitutive manner may be performed with any of the procedures. It is preferable that lipofection method which does not cause injury to the cell when an exogenous DNA is introduced. Any reagents known to a person skilled in the art may be used as the reagents used in the procedures. Other than MultiFectam used in the examples of this specification commercially available reagents, X-tremeGENE 9, FuGENE 6, Lipofectin, Lipofectamine, and the like may be used. In the present invention, the neurodegenerative disease for preparation of insoluble fractions and the neurodegenerative-disease-related proteins expressed in the cells may be the same or different.

In the present invention, with regard to obtaining the culture cell expressing the neurodegenerative-disease-related protein in a constitute manner and the introduction of the insoluble fractions into the culture cell, a culture container size, a cultured cell number, an amount of introducing the insoluble fraction and the like may be scaled up, provided that some effects similar to the examples are provided.

In a method of examining a cytotoxicity in the present invention, the term "cytotoxicity" indicates that cell cytoplasm is released to the medium by destruction of the cell membrane, the cytotoxicity may be quantified by the loss of ability to exclude a dye and the detection of activity of enzyme such as LDH (lactase dehydrogenase) in the medium, wherein the LDH is located in the cell cytoplasm in a normal condition.

In a method of screening in the present invention, a candidate compound for promoting or suppressing the insoluble aggregates include, but are not limited to: a compound prepared from a microorganism, fungus, plant and animal and a compound synthesized chemically. The compound for promoting the formation of the insoluble aggregates is necessary for performing a risk management with regard to an increase of the neurodegenerative disease and for elucidation of the pathological mechanism of the disease. The compound for suppressing the formation of the insoluble aggregates may be utilized to the development of useful medicines for preventing, treating, ameliorating and suppressing the progression of pathological condition of neurodegenerative disease, and so on.

With regard to the animal species of the neurodegenerative-disease-related protein, the culture cell, the insoluble fraction and the biological sample in the present invention may be a combination of any animal species, provided that a new insoluble aggregate is formed from the neurodegenerative-disease-related protein expressing in the cultured cell where the introduced insoluble fraction works as a seed. The animal species may be selected from the group comprising, as other than a human, a mammal and a primate, wherein the mammal includes a model animal available to produce a transgenic animal, e.g. mouse, rat, rabbit and goat etc., and the primates such as *Macaca mulatta* available to an application of ES cell are included. There may be a case as that, when the insoluble fraction originated from the brain of patient is utilized, a cultured cell expressing the human neurodegenerative-disease-related proteins is used. While, in the case where the cultured cell expressing the human neurodegenerative-disease-related protein is utilized, the cell may be originated from any animal species other than human. The cultured cell derived from a knockout animal in which e.g. a protein kinase, a proteinase and the like are knocked out may be used.

In the present invention, a "biological sample" refers to all of the biological samples having a possibility to comprise an insoluble fraction which works as a nucleus for forming aggregates of the neurodegenerative-disease-related protein, and the biological samples include a body fluid, an organ and a tissue wherein the body fluid include, but are not limited to: a spinal fluid, blood, blood plasma, lymph fluid and seminal fluid, and the organ and the tissue include, but are not limited to: the brain, spinal cord, bone marrow and thymus. Preferably, the biological samples are the brain and the spinal fluid.

All the documents referred to in this specification are incorporated as the citations of the original documents.

BRIEF DESCRIPTION OF THE DRAWINGS

FIG. 1-2 is a Western blot image of HA-TDP expressing cells introduced an insoluble fraction originated from an ALS patient.

FIG. 1-3 is a Western blot image of HA-TDP expressing cells introduced an insoluble fraction originated from an ALS patient.

FIG. 2-1 is a Western blot image of αS expressing cell introduced an insoluble fraction originated from an ALS patient.

FIG. 2-2 is a Western blot image of αS expressing cell introduced an insoluble fraction originated from an ALS patient.

FIG. 3-1 is a combination of confocal microscopic photographs of the cultured cells stained immunocytochemically to detect insoluble aggregates accumulated by insoluble fraction originated from the brain of an ALS patient.

FIG. 3-2 is a combination of confocal microscopic photographs of the cultured cells stained immunocytochemically to detect insoluble aggregates accumulated by insoluble fraction originated from the brain of an ALS patient.

FIG. 3-3 is a combination of confocal microscopic photographs of the cultured cells stained immunocytochemically to detect insoluble aggregates accumulated by insoluble fraction originated from the brain of an ALS patient.

FIG. 3-4 is a combination of confocal microscopic photographs of the cultured cells stained immunocytochemically to detect insoluble aggregates accumulated by insoluble fraction originated from the brain of an ALS patient.

FIG. 4-1 is a Western blot image of αS expressing cells introduced an insoluble fraction originated from a DLB patient.

FIG. 4-2 is a Western blot images of αS expressing cells introduced an insoluble fraction originated from a DLB patient.

FIG. 4-3 is a combination of confocal microscopic photographs of the cultured cells stained immunocytochemically to detect insoluble aggregates accumulated by insoluble fraction originated from brain of a DLB patient.

FIG. 5-1 is a Western blot image of HA-3R1N expressing cells introduced an insoluble fraction originated from a PSP patient.

FIG. 5-2 is a Western blot image of HA-4R1N expressing cells introduced an insoluble fraction originated from a PSP patient.

FIG. 5-3 is a Western blot image of HA-4R1N expressing cells introduced an insoluble fraction originated from a CBC patient.

FIG. 5-4 is a Western blot image of HA-3R1N expressing cells introduced an insoluble fraction originated from a Pick's disease patient.

FIG. 7-1 is a Western blot image of HA-TDP expressing cells introduced an insoluble fraction and detected with anti-HA antibody.

FIG. 7-2 is a Western blot image of HA-TDP expressing cells introduced an insoluble fraction and detected with anti-phosphorylated TDP antibody.

MODE FOR CARRYING OUT THE INVENTION

Figure 1:
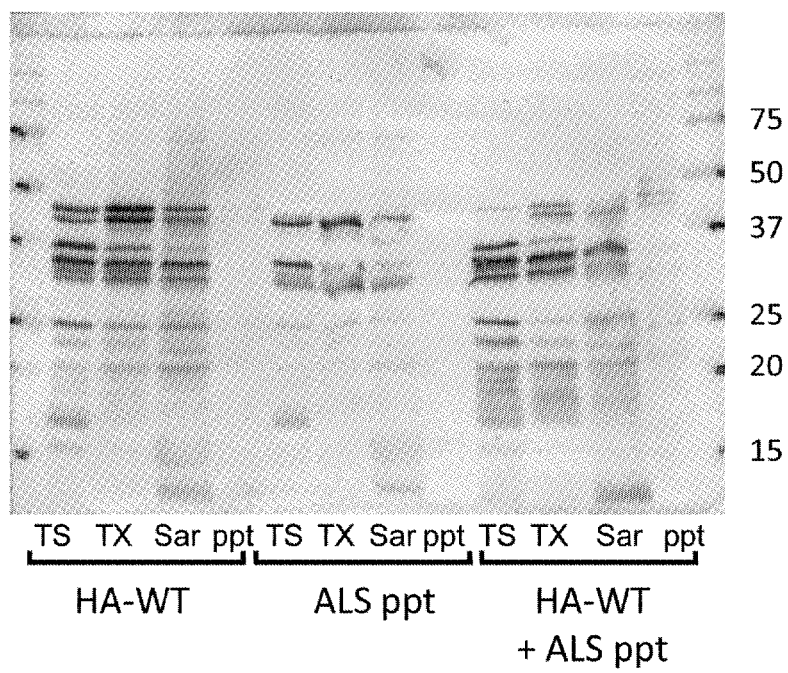
FIG. 1-1 is a Western blot image of HA-TDP expressing cells introduced an insoluble fraction originated from an ALS patient.

Examples of the present invention described below are intended only to exemplify the invention rather than to limit the scope thereof. The scope of the present invention is limited only by the description in claims. In fact, the present invention can be modified through addition, elimination and substitution of constituent features, without departing from the gist of the invention.

Example 1

1. Materials and Methods
1.1 Harvest of Samples
The following experiments in these examples were performed based on an approval of research ethics committee of Tokyo Metropolitan Institute of Medical Science (the former Tokyo Institute of Psychiatry) (approval number: 17-36, approval date: 2005.9.3).

1.2 Preparation of Insoluble Fractions from Brain Samples

The frozen brain samples harvested from the patients (0.5 g) were homogenated in five times its volume of A68 buffer (10 mM Tris (pH7.5), 0.8 M NaCl, 1 mM EGTA, 1 mM DTT) and their suspensions were prepared. N-sodium lauroyl sarcosinate was added to the suspensions at a final concentration of 1% and incubated at 37° C. for 30 min. The suspensions were centrifuged (12,000×g, 10 min, 25° C.), and the supernatants were collected. Further, the suspensions were centrifuged (100,000×g, 20 min, 25° C.), and a precipitate was obtained. The precipitate was treated by ultrasonication in PBS using Biomic 7040 Ultrasonic Processor (Seiko Corporation), and about 500 μL of the precipitate sample was dispensed in an eppendorf tube. The supernatant was removed after centrifugation (100,000×g, 20 min, 25° C.), and the insoluble fractions from ALS patients were prepared.

1.3 Preparation of Sample for Introducing into the Cells

PBS (150 μL) was added to the insoluble fractions, and ultrasonication treatment was performed with VP-5S type device (Titech Corporation). The supernatant was collected after centrifugation (2,300×g, 5 min, 25° C.). Five μL of the supernatant was dispensed in an 1.5 mL eppendorf tube to introduce into the cultured cells in one well of 6-well plate, and MultiFectam (Promega Corporation) (62.5 μL) and OptiMEM (Life Technologies Japan Ltd.) (120 μL) per each tube were added, then incubated at ambient temperature for 30 min. The OptiMEM (62.5 μL) were further added and incubated at ambient temperature for 5 min. The total of the sample obtained for introducing into the cells was introduced into cultured cells inoculated in one well of a 6-well plate.

1.4 Cultured Cells

As cultured cells, SH-SY5Y cells of neuroblastoma cell line and its transfectant transiently expressing a desired protein were used. The SH-SY5Y cells were cultured with a cell culture medium (D-MEM/F-12, Life Technologies Japan Ltd.) containing 10% fetal calf serum. Hereinafter, if not otherwise defined, the SH-SY5Y cells and the transfectants were cultured in a 5% $CO_2$ and saturated water vapor atmosphere at 37° C. The SH-SY5Y cells were inoculated in a commercially available 6-well plate under a condition so that the cells became to 30% to 50% confluent in the well in the next day.

1.5 Preparation of Transfectants

Two transfectants of (1) SH-SY5Y cells expressing human α-synuclein (hereinafter referred to as "αS expressing cells" for transfectants and "αS" for the human α-synuclein, respectively) and (2) SH-SY5Y cells expressing HA-tagged TAR DNA binding protein (hereinafter referred to as "HA-TDP expressing cells" for the SH-SY5Y cells and an "HA-TDP" HA-tagged TAR DNA binding protein, respectively) were prepared. In brief, a construct in which a polynucleotide encoding αS or HA-TDP was inserted into pcDNA3 vector were prepared (Ueda. K et al., Proc. Natl. Acad. Sci. U.S.A. 90: 11282 (1993), Ou. S H et al., J Virol. 3584: 394 (1995)). Mixture of the construct (1 μg), X-tremeGENE 9 DNA transfection reagent (Roche Diagnostics K.K.) (3 μL) and the OptiMEM (100 μL) was added to 30% to 50% confluent of the SH-SY5Y cells and incubated over night, then used in the following step of introduction of insoluble fraction.

1.6 Introduction of Insoluble Fraction into the Cultured Cells

An amount of sample for introduction per one well of the 6-well plate was added to the cell culture medium of one well, then the cultured cells was incubated for 6 hours. After the incubation, the medium was replaced with a flesh cell culture medium (2 mL) and the cultured cells were incubated for 3 days. Then, the cultured cells were used to perform the analysis by Western blotting and immunocytochemistry. If the cultured cells were not used immediately, the cultured cells were stored at −20° C.

1.7 Analysis by Western Blotting

1.7.1 Preparation of Various Cell Extract Fractions

After the introduction of insoluble fraction into the cultured cells, the cell culture medium was removed and 1 mL of PBS was added. The cultured cells were scraped and centrifuged (1.800×g, 5 min, 4° C.). After removal of supernatant, 1 mL of PBS was added. The cultured cells were centrifuged (1,800×g, 5 min, 4° C.) again and washed.

1.7.2 Preparation of Tris Buffer Soluble Fraction

The cultured cells were suspended in 100 μL of a cell lysis buffer (50 mM Tris-HCl (pH 7.5), 0.15 M NaCl, 5 mM EDTA, 5 mM EGTA and protease inhibitor cocktail set III (catalogue No. 539134, Merck & Co., Inc.)), and incubated at 37° C. for 30 min. After ultrasonication treatment using VP-5S type device (Titech Corporation), the supernatant and precipitate were separated by ultracentrifugation (290,000× g, 20 mM, 4° C.), the supernatant was used as Tris buffer soluble fraction (hereinafter referred to as "TS fraction").

1.7.3 Preparation of Tris Buffer Soluble Fraction Containing Triton X-100

The precipitate obtained in a preparation of TS fraction was suspended in 100 μL of the cell lysis buffer containing 1% Triton X-100, and incubated at 37° C. for 30 min. After ultrasonication treatment using VP-5S type device (Titech Corporation), the supernatant and precipitate were separated by ultracentrifugation (290,000×g, 20 min, 4° C.), the supernatant was used as Tris buffer soluble fraction containing Triton X-100 (hereinafter referred to as "TX fraction").

1.7.4 Preparation of Fractions Soluble and Insoluble to Tris Buffer Containing N-Sodium Lauroyl Sarcosinate The precipitate obtained in the preparation of TX fraction was suspended in a cell lysis buffer containing 1% N-sodium lauroyl sarcosinate, and incubated at 37° C. for 30 min. After ultrasonication treatment using VP-5S type device (Titech Corporation), the supernatant and precipitate were separated by ultracentrifugation (290,000×g, 20 min, 4° C.), the supernatant was used as Tris buffer soluble fraction containing N-sodium lauroyl sarcosinate (hereinafter referred to as "Sar fraction"). And also, the precipitate was used as insoluble fraction (hereinafter referred to as "ppt fraction").

1.7.5 Western Blotting

TS, TX, Sar and ppt fractions were used in the Western blotting by standard method well known to those skilled in the art. In brief, each fraction was separated by electrophoresis with 13.5% SDS-polyacrylamide gel, respectively. The separated proteins were transferred to a PVDF membrane, reacted with the following primary and secondary antibodies, and detected with an ECL Plus Western Blotting Detection System (GE Healthcare Japan Corporation) and an ImageQuant™ LAS 4000 mini (GE Healthcare Japan Corporation).

The primary antibodies used and their dilution rates were as follows:

(1) anti-TDP antibody recognizing TDP monomer (catalogue No. 60019-2-Ig, ProteinTech, TRANS GENIC INC., hereinafter referred to as "anti-TDP monomer antibody"), 1:1,000 dilution.

(2) anti-HA antibody recognizing HA-tag (catalogue No. H9658, Sigma-Aldrich Japan Inc.) (hereinafter referred to as "anti-HA"), 1:2,000 dilution.

(3) anti-TDP antibody recognizing TDP of phosphorylated serine 409/410 (TDP43-pS409/410, International Patent Organism Depositary, National Institute of Advanced Industrial Science and Technology, recipient number: FERM ABP-10984, WO2009/008529) (hereinafter referred to as "anti-409/410"), 1:1,000 dilution.

(4) antibody recognizing α-synuclein and β-synuclein (anti-Syn102 antibody, Nonaka T et al., Biochemistry, 44: 361 (2005)) (hereinafter referred to as "anti-102 antibody"), 1:2,000 dilution.

(5) anti-α-synuclein antibody recognizing phosphorylated serine 129 (Fujiwara H et al., Nat. Cell Biol. 4: 160 (2002)) (hereinafter referred to as "anti-Pser129 antibody"), 1:2,000 dilution.

(6) anti-synuclein antibody recognizing peptide of 131 to 140 amino acids of synuclein as antigen (Masuda M et al., FEBS Lett. 583: 787 (2009)) (hereinafter referred to as "131-140 antibody"), 1:1,000 dilution.

The secondary antibodies used and their dilution rates were as follows:

(1) anti-rabbit HRP labeled IgG (catalogue No. 170-6515, Bio-Rad Laboratories, Inc.), 1:20,000 dilution.

(2) anti-mouse HRP labeled IgG (catalogue No. 170-6516, Bio-Rad Laboratories, Inc.), 1:20,000 dilution.

(3) biotinylated anti-rabbit IgG (catalogue No. BA1000, Funakoshi Co., Ltd.), 1:500 dilution.

(4) biotinylated anti-mouse IgG (catalogue No. BA2000, Funakoshi Co., Ltd.), 1:500 dilution.

1.8 Observation by Confocal Microscopy

An immunocytochemical staining was performed by standard method well known to those skilled in the art. In brief, the cultured cells were fixed with 4% paraformaldehyde. Then, permeation treatment was performed with 0.2% Triton X-100 and blocking treatment was performed with PBS containing 5% fetal calf serum. The anti-HA and anti-409/410 antibodies were suitably diluted and used as primary antibodies. Alexa Fluor 488 goat anti-rabbit IgG (catalogue No. A11008, Invitrogen Corporation) and Alexa Fluor 568 goat anti-mouse IgG (A11004, Invitrogen Corporation) were suitably diluted and used as secondary antibodies. The nuclei of the cells were stained with TO-PRO-3 (Molecular Probes, Life Technologies Japan Ltd.). The cultured cells were embedded with ProLong Gold antifade reagent (catalogue No. P36934, Invitrogen Corporation), and observed with a confocal microscope (Carl Zeiss Microscopy Co., Ltd.).

2. Results

2.1 Western Blotting

Figures 1, 2:
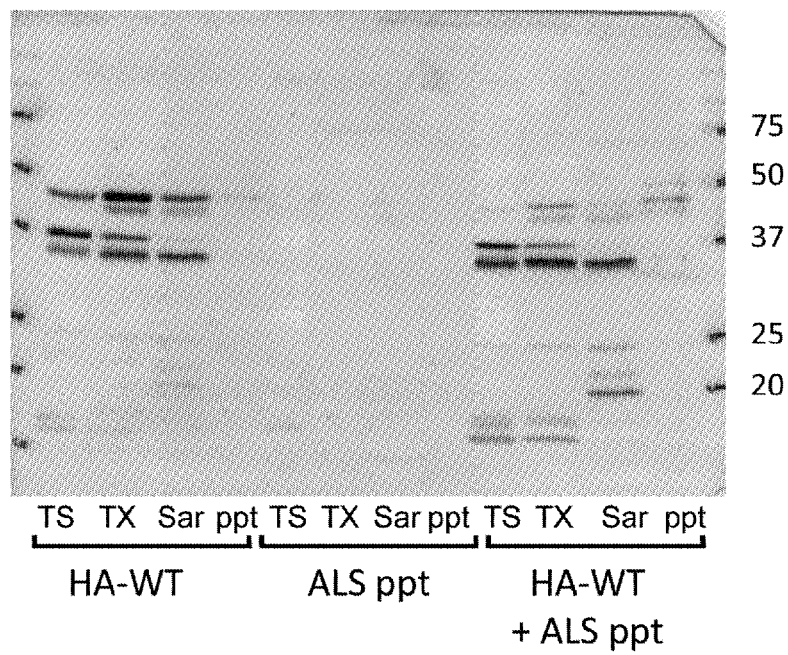
Figures 1, 2, 3:
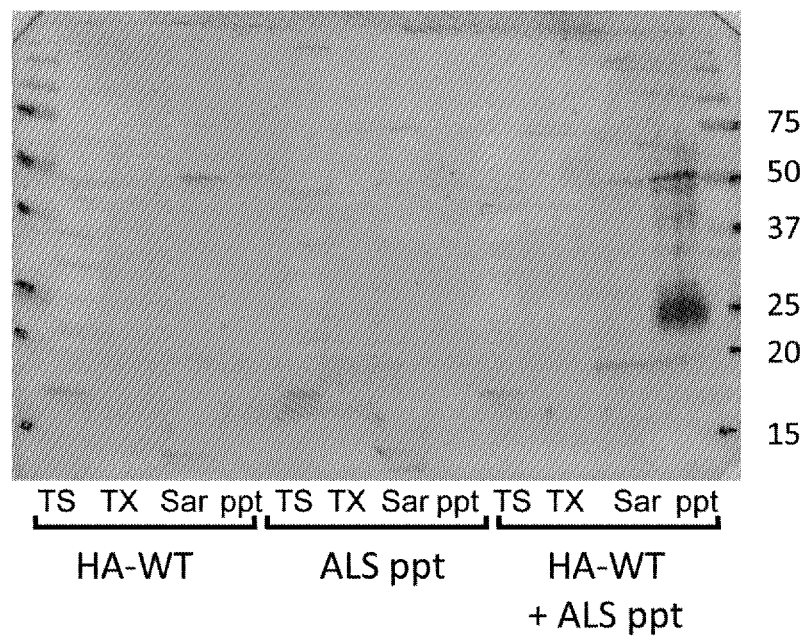
Figures 1, 2:
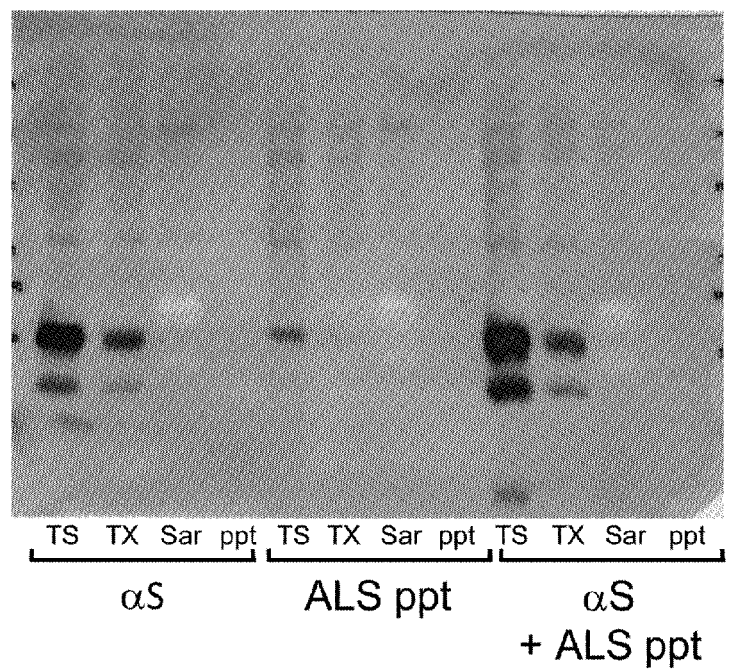
Figure 2:
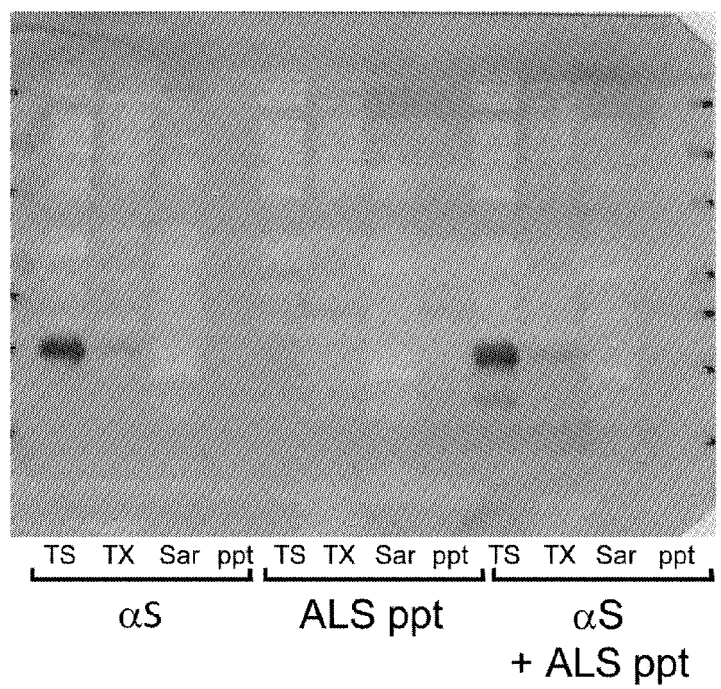

FIGS. 1-1, 1-2 and 1-3 are Western blot images of HA-TDP expressing cell fractions prepared by introducing the insoluble fraction originated from the ALS patient into the HA-TDP expressing cells, and detected with each of anti-TDP monomer antibody, anti-HA and anti-409/410 antibody, respectively. A term "HA-WT" indicates HA-TDP expressing cells without introducing the insoluble fraction originated from the brain of patient. A term "ALS ppt" indicates that the insoluble fraction from the brain of ALS patient was introduced into untransfected SH-SY5Y cells. A term "HA-WT ALS ppt" indicates that the insoluble fraction from the brain of ALS patient was introduced to HA-TDP expressing cells. Terms "TS", "TX", "Sar" and "ppt" indicate that TS, TX, Sar and ppt fractions of the cells treated under the condition of "HA-WT", "ALS ppt" or "HA-WT+ ALS ppt" were applied to each lane. As can be seen in FIGS. 1-1, 1-2 and 1-3, anti-TDP monomer antibody, anti-HA and anti-409/410 antibodies did not respond to the ppt fraction of HA-TDP expressing cells and the ppt fraction of SH-SY5Y cells introduced the insoluble fraction from the brain of ALS patient. However, the anti-TDP monomer antibody, anti-HA and anti-409/410 antibodies responded to the ppt fraction of HA-TDP expressing cells introduced the insoluble fraction from the brain of ALS patient. Particularly, the anti-409/410 antibody detected about 50 kDa intact TDP and about 25 kDa C-terminal fragment of TDP. This cross-reactivity was similar to the cross-reactivity detected in Western blotting of sample originated from neurodegenerative disease patients, remarkably ALS patient.

FIGS. 2-1 and 2-2 are Western blot images of αS expressing cell fractions wherein the fractions were prepared by introducing the insoluble fraction originated from the ALS patient into the αS expressing cells, and detected with each of anti-Syn102 antibody and anti-PSer129 antibody, respectively. The term "αS" indicates αS expressing cells not introduced the insoluble fraction originated from the brain of patient. The term "ALS ppt" indicates that the insoluble fraction from the brain of ALS patient was introduced into untransfected SH-SY5Y cells. The term "αS+ALS ppt" indicates that the insoluble fraction from the brain of ALS patient was introduced into αS expressing cells. Terms "TS", "TX", "Sar" and "ppt" indicate that TS, TX, Sar and ppt fractions of the cells treated under the condition of "αS", "ALS ppt" or "αS+ALS ppt" were applied to each lane. As can be seen in FIGS. 1-1, 1-2 and 1-3, anti-Syn102 antibody and anti-PSer129 antibody did not respond to ppt fraction of αS expressing cells, ppt fraction of SH-SY5Y cells introduced the insoluble fraction from the brain of ALS patient, ppt fraction of αS expressing cells introduced the insoluble fraction from the brain of ALS patient.

From the above results, it was demonstrated that the insoluble fraction from the brain of ALS patient significantly promoted an accumulation of insoluble aggregates in the HA-TDP expressing cells, while the insoluble fraction did not promote the accumulation of insoluble aggregates in the αS expressing cells. Accordingly, it was shown that, for accumulation of insoluble aggregates, a specific combination of the insoluble fraction to become a nucleus (seed) of aggregation and protein monomers to form insoluble aggregates was needed.

2.2 Observation by Confocal Microscopy

Figures 1, 3:
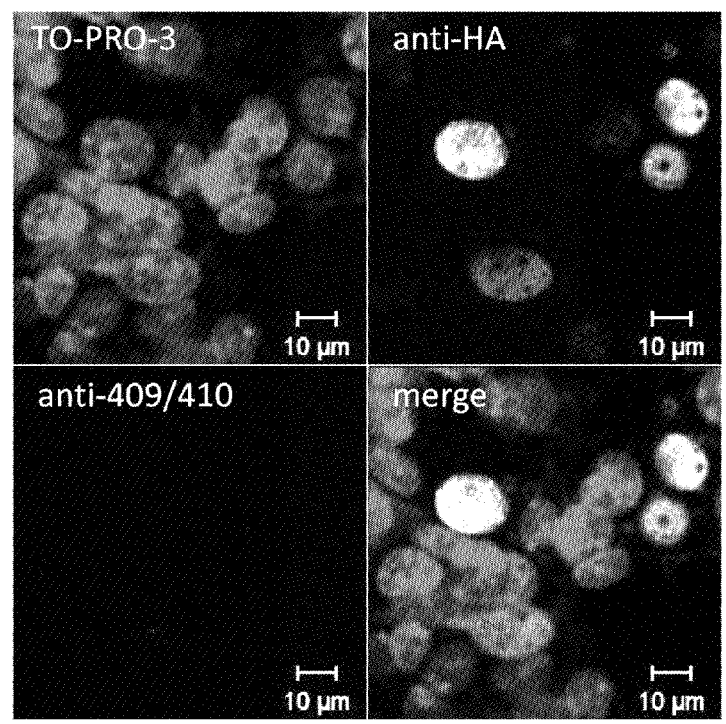
Figures 2, 3:
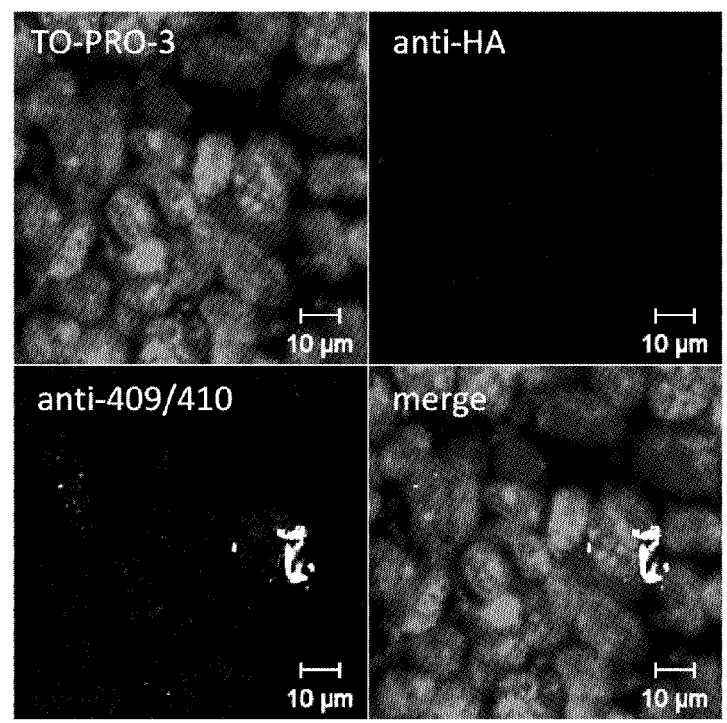
Figure 3:
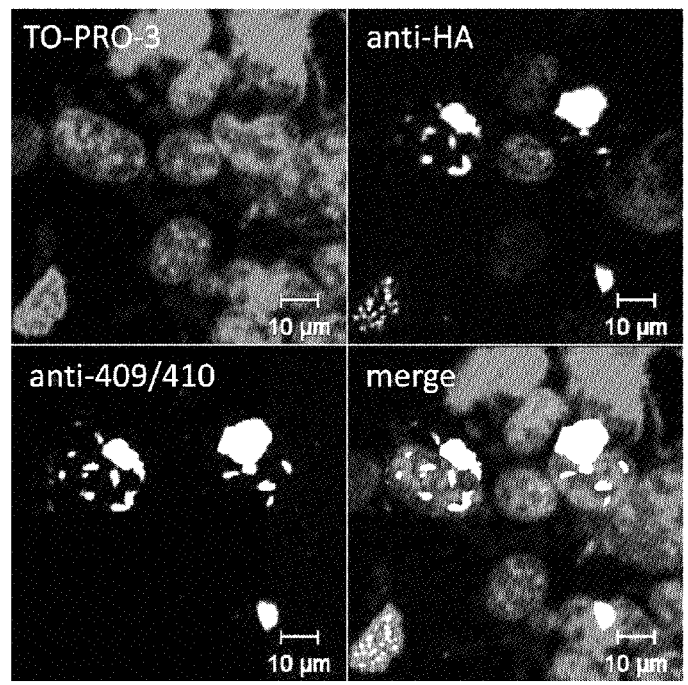
Figures 3, 4:
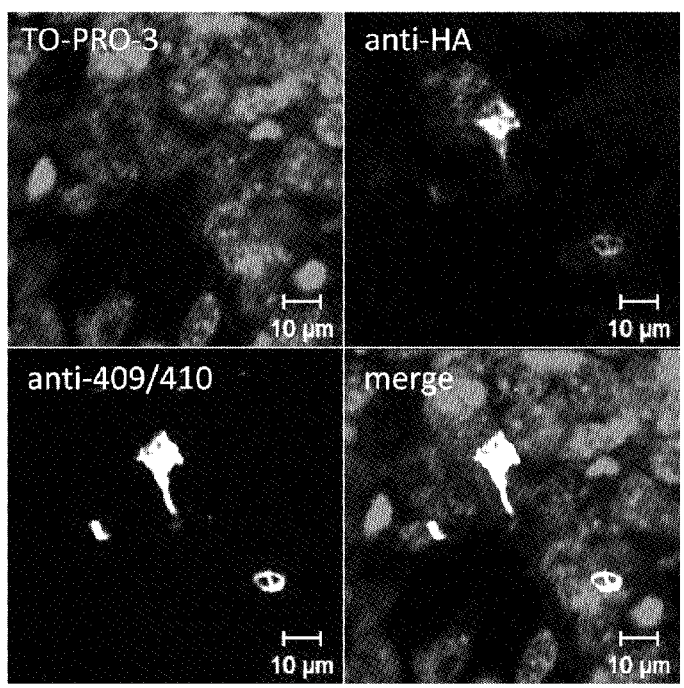
Figures 1, 4:
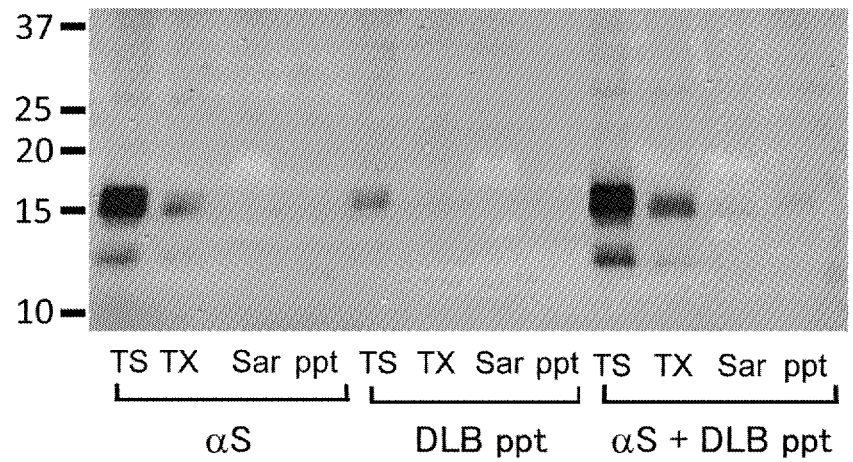
Figures 2, 4:
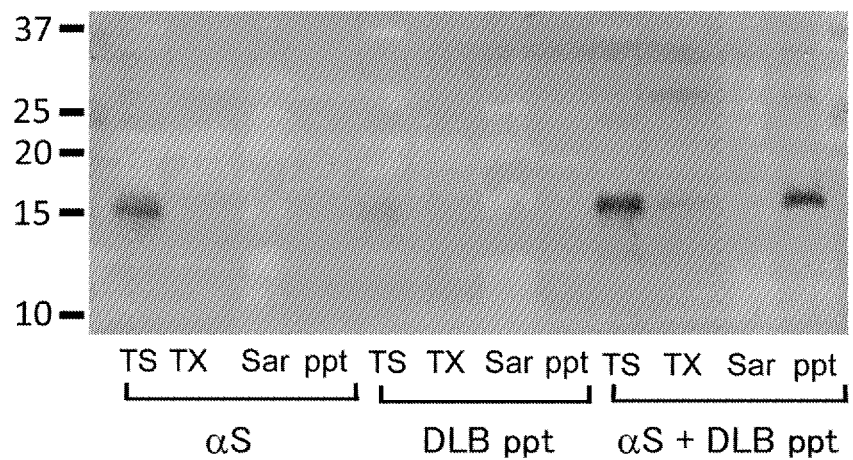
Figures 3, 4:
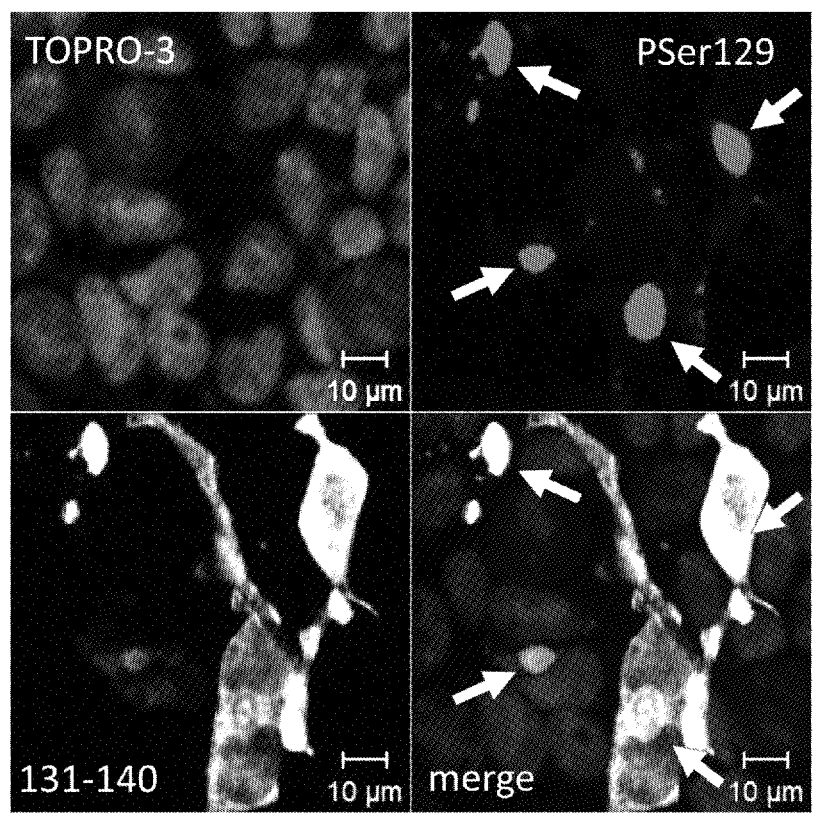

FIGS. 3-1, 3-2, 3-3 and 3-4 are a combination of confocal microscopic photographs of the cultured cells stained immunocytochemically to detect insoluble aggregates accumulated by insoluble fraction originated from the brain of an ALS patient. The primary antibody used was indicated on the upper-left in each photograph of figures. The term "merge" refers to the image merged by the other three photographs. The HA-TDP expressing cells were used in FIGS. 3-1, 3-3 and 3-4, and SH-SY5Y cells were used in FIG. 3-2. In FIG. 3-1, the insoluble fraction was introduced, and in FIGS. 3-2, 3-3 and 3-4, the insoluble fraction originated from ALS patient was introduced. From FIG. 3-1, phosphorylated TDP was not detected in the HA-TDP expressing cells into which the insoluble fraction originated from the ALS patient had not been introduced. From FIG. 3-2, phosphorylated TDP was slightly detected in SH-SY5Y cells into which the insoluble fraction originated from the ALS patient had been introduced. From FIGS. 3-3 and 3-4, localization patterns of phosphorylated TDP and HA-TDP were overlapped in HA-TDP expressing cells introduced the insoluble fraction originated from the ALS patient. In FIG. 3-4, the cells expressed phosphorylated TDP and HA-TDP had an unique diamond shape.

Example 2

1. Materials and Methods 1.1 Combination of Insoluble Aggregates and Neurodegenerative-Disease-Related Proteins The harvest of samples, preparation of insoluble fractions from the brain samples, preparation of samples for introduction including the insoluble fractions, cell culturing, preparation of transfectants, introduction of the insoluble fractions into the cultured cells, Western blotting and confocal microscopic observation were performed in accordance with the procedures similar to those in the example 1. The brain sample was obtained from the patient having each of dementia with Lewy bodies (DLB), progressive supranuclear palsy (PSP), corticobasal degeneration (CBD), Pick's disease or frontotemporal lobar degeneration (FTLD), then each of the insoluble fraction was prepared. In addition, the two kinds of transfectants were prepared i.e., (1) one transfectant of SH-SY5Y cells expressing an HA-tagged isoform of microtubule associated protein; tau having three repeated sequences (hereinafter referred to as "HA-3R1N" for the isoform, and referred to as "HA-3R1N expressing cells" for the cells) and (2) another transfectant was SH-SY5Y cells expressing another HA-tagged isoform of microtubule associated protein; tau having four repeated sequences (hereinafter referred to as "HA-4R1N" for the isoform, and referred to as "HA-4R1N expressing cells" for the cells). In brief, a constract inserted with nucleotides encording HA-3R1N or HA-4R1N into pcDNA3 vector was prepared. (Goedert M et al., Neuron 3: 519(1989) The mixture of the construct (1 µg), X-tremeGENE 9 DNA transfection reagent (Roche Diagnostics K.K.) (3 µL) and the OptiMEM (100 µL) was added to the SH-SY5Y cells of 30% to 50% confluent and incubated over night, then used in the following step of introduction of the insoluble fractions. As a primary antibody, an anti-tau antibody recognizing phosphorylated serine 396 (catalogue No. 577815, Merck & Co., Inc.) (hereinafter referred to as "anti-PS396 antibody"), as a secondary antibody, anti-rabbit HRP labeled IgG (catalogue No. 170-6515, Bio-Rad Laboratories, Inc.), 1:20,000 dilution or biotinylated anti-mouse IgG (catalogue No. BA2000, Funakoshi Co., Ltd.), 1:500 dilution were further used in Western blotting.

1.2 Cytotoxicity Examination

Cytotoxicity examination was performed in accordance with the manufacturer's instruction using a commercially available cytotoxicity examination kit (CytoTox 96 (registered trademark) Non-Radioactive Cytotoxicity Assay, G1780, Promega Corporation) to SH-SY5Y cells, and HA-TDP expressing cells introduced the insoluble fraction from the patient of ALS, FTLD or Pick's disease. A cytotoxicity ratio (%) was calculated as percentage of quotient obtained by dividing a measurement value of lactase dehydrogenase in the cells culture medium by a measurement value of lactase dehydrogenase in both of the cell culture medium and living cells.

2. Results

FIGS. 4-1 and 4-2 are Western blot images of αS expressing cell fractions prepared by introducing the insoluble fraction from the DLB patient into the αS expressing cells, and detected with each of anti-Syn102 antibody and anti-PSer129 antibody, respectively. The term "αS" indicates the αS expressing cells without introducing an insoluble fraction from the brain of patient. The term "DLB ppt" indicates that the insoluble fraction from the brain of DLB patient introduced into untransfected SH-SY5Y cells. The term "αS+DLB ppt" indicates that the insoluble fraction from the brain of DLB patient was introduced into αS expressing cells. Terms "TS", "TX", "Sar" and "ppt" indicate that TS, TX, Sar and ppt fractions of the cells treated under the condition of the "αS", "DLB ppt" and "αS+DLB ppt" were applied to each lane, respectively. As can be seen in FIGS. 4-1 and 4-2, anti-Syn102 antibody did not respond to the ppt fraction of αS expressing cells, the ppt fraction of SH-SY5Y cells introduced the insoluble fraction from the DLB patient, ppt fraction of αS cells introduced insoluble fraction from the DLB patient. The anti-PSer129 antibody did not respond to ppt fraction of αS expressing cells and ppt fraction of SH-SY5Y cells introduced the insoluble fraction from the DLB patient, but responded to the ppt fraction of αS expressing cells introduced the insoluble fraction from the DLB patient. From these results, in the αS expressing cells, most of αS was present in the soluble fractions and the quantity of insoluble aggregate was very small, when the insoluble fractions from the DLB patient had been introduced or not. However, in the αS expressing cells introduced the insoluble fraction from the DLB patient, a significant amount of phosphorylated αS transferred to the insoluble fraction. The phosphorylated αS was not detected in untransfected SH-SY5Y cells introduced the insoluble fraction originated from the brain of DLB patient, thus it was suggested that the insoluble fraction from the DLB patient works as seeds, and new insoluble aggregates were formed in αS expressing cells introduced the insoluble fraction from the DLB patient.

FIG. 4-3 is a combination of confocal microscopic photographs of the cultured cells stained immunocytochemically to detect insoluble aggregates accumulated by the insoluble fraction originated from the brain of the DLB patient. The primary antibody used was indicated on the upper-left in each photograph of figure. The term "merge" refers to the image merged by the other three photographs. In αS expressing cells introduced the insoluble fraction originated from the DLB patient αS itself was detected as overall localization in the cytoplasm, but a localization of the phosphorylated αS was detected at an inclusion body.

Figures 1, 5:
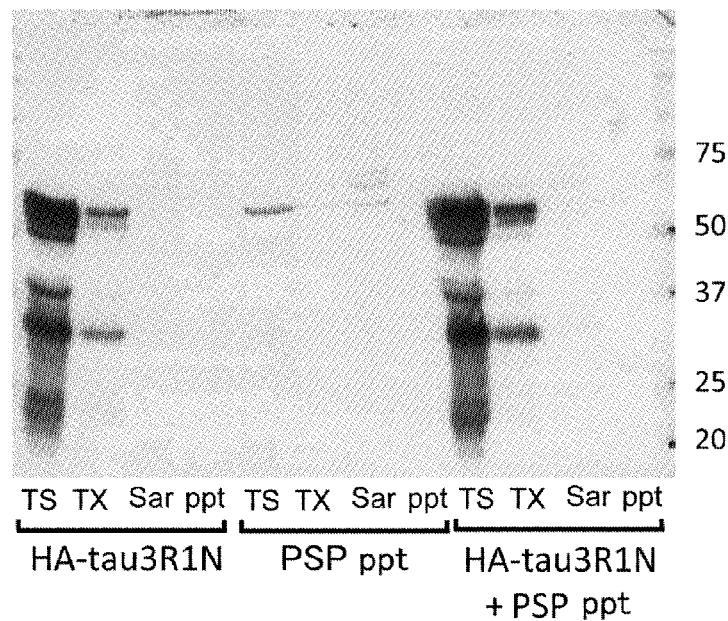
Figures 2, 5:
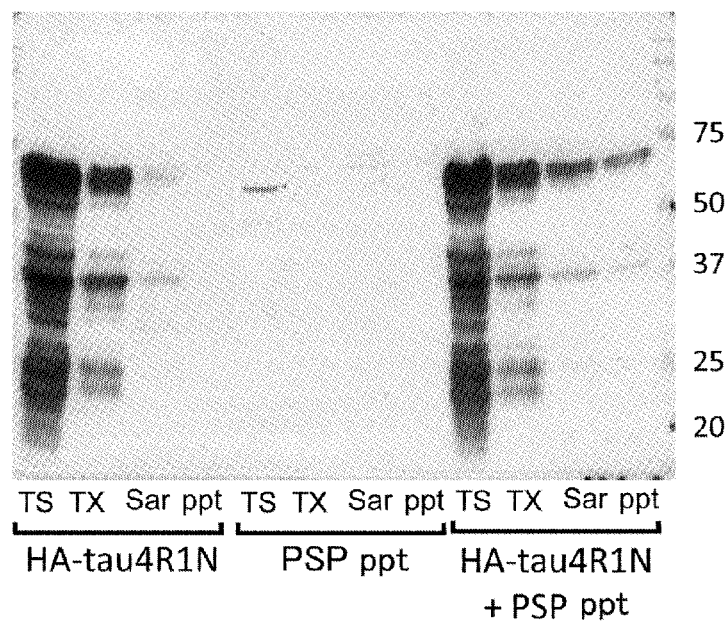
Figures 3, 5:
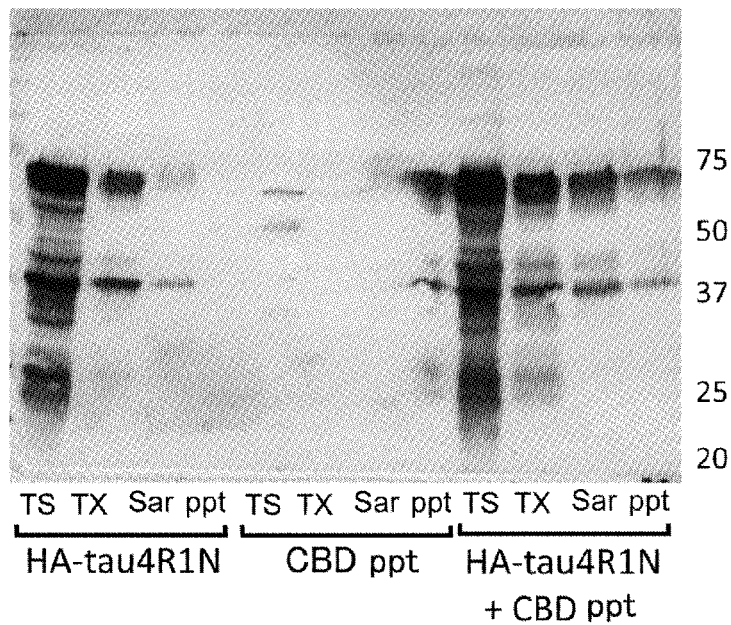
Figures 4, 5:
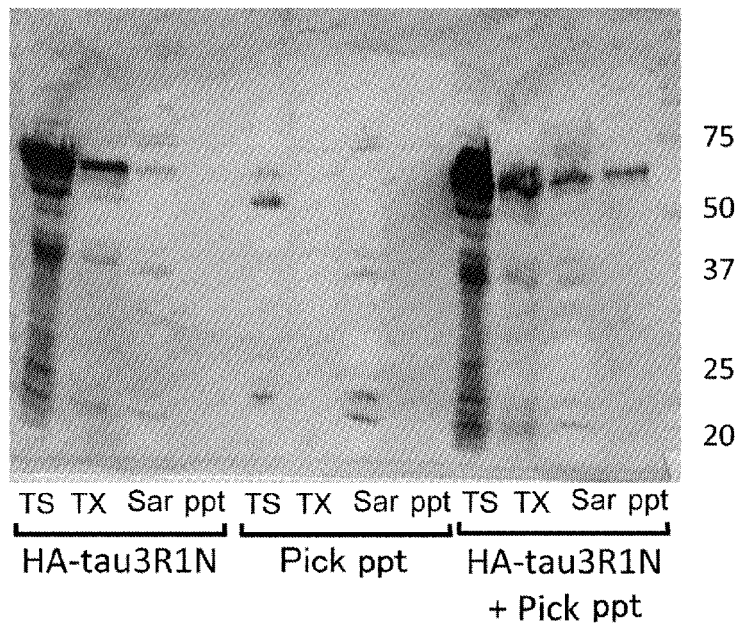

FIG. 5-1 is a combination of Western blot images of HA-3R1N expressing cells fractions prepared by introducing the insoluble fraction from the PSP patient into the HA-3R1N expressing cells, and detected with anti-PS396 antibody, respectively.

The term "HA-tau3R1N" indicates a HA-3R1N expressing cells into which the insoluble fraction from the brain of patient had not been introduced. The term "PSP" indicates that the insoluble fraction from the brain of PSP patient had introduced into an untransfected SH-SY5Y cells. The term "HA-tau3R1N+PSP" indicates a HA-3R1N expressing cells into which the insoluble fraction from the brain of PSP patient had been introduced. Terms "TS", "TX", "Sar" and "ppt" indicate that TS, TX, Sar and ppt fractions of the cells treated under the condition of the "HA-tau3R1N", "PSP" and "HA-tau3R1N+PSP" were applied to each lane, respectively. As can be seen in FIG. 5-1, anti-PS396 antibody did not respond to ppt fraction of HA-3R1N expressing cells, ppt fraction of SH-SY5Y cells introduced the insoluble fraction from the PSP patient and ppt fraction of HA-3R1N cells introduced the insoluble fraction from the PSP patient.

FIG. 5-2 is a combination of Western blot images of HA-4R1N expressing cell fractions prepared by introducing an insoluble fraction from the PSP patient into the HA-4R1N expressing cells, and detected with anti-PS396 antibody, respectively. The term "HA-tau4R1N" indicates a HA-4R1N expressing cells into which the insoluble fraction originated from the brain of patient had not been introduced. The term "PSP" indicates that the insoluble fraction originated from the brain of PSP patient had been introduced into untransfected SH-SY5Y cells. The term "HA-tau4R1N+PSP" indicates HA-4R1N expressing cells into which the insoluble fraction originated from the brain of PSP patient had been introduced. Terms "TS", "TX", "Sar" and "ppt" indicate that TS, TX, Sar and ppt fractions of the cells treated under the condition of the "HA-tau4R1N", "PSP" and "HA-tau4R1N+PSP" were applied to each lane, respectively. As can be seen in FIG. 5-2, anti-PS396 antibody did not respond to the ppt fraction of HA-4R1N expressing cells and the ppt fraction of SH-SY5Y cells introduced the insoluble fraction originated from the PSP patient, while the antibody responded to the ppt fraction of HA-4R1N cells introduced the insoluble fraction from the PSP patient.

FIG. 5-3 is a combination of Western blot images of HA-4R1N expressing cells fraction prepared by introducing the insoluble fraction originated from the CBD patient into the HA-4R1N expressing cells, and detected with anti-PS396 antibody, respectively. The term "HA-tau4R1N" indicates that HA-4R1N expressing cells into which the insoluble fraction from the brain of patient had not been introduced. The term "CBD" indicates that the insoluble fraction from the brain of CBD patient had introduced into an untransfected SH-SY5Y cells. The term "HA-tau4R1N+CBD" indicates that the insoluble fraction originated from the brain of CBD patient had introduced into the HA-4R1N expressing cells. Terms "TS", "TX", "Sar" and "ppt" indicate that TS, TX, Sar and ppt fractions of the cells treated under the condition of the "HA-tau4R1N", "CBD" and "HA-tau4R1N+CBD" were applied to each lane, respectively. As can be seen in FIG. 5-3, anti-PS396 antibody did not respond to the ppt fraction of HA-4R1N expressing cells and the ppt fraction of SH-SY5Y cells introduced the insoluble fraction from the CBD patient, while the antibody responded to the ppt fraction of HA-4R1N cells introduced the insoluble fraction from the CBD patient.

FIG. 5-4 is a combination of Western blot images of HA-3R1N expressing cell fraction prepared by introducing the insoluble fraction from the Pick disease patient into the HA-3R1N expressing cells, and detected with anti-PS396 antibody, respectively. The term "HA-tau3R1N" indicates HA-4R1N expressing cells into which the insoluble fraction from the brain of patient had not been introduced. The term "Pick" indicates that the insoluble fraction from the brain of Pick patient was introduced into untransfected SH-SY5Y cells. The term "HA-tau3R1N+Pick" indicates HA-4R1N expressing cells into which an insoluble fraction originated from the brain of Pick disease patient had introduced. Terms "TS", "TX", "Sar" and "ppt" indicate that TS, TX, Sar and ppt fractions of the cells treated under the condition of the "HA-tau3R1N", "Pick" and "HA-tau3R1N+Pick" were applied to each lane, respectively. As can be seen in FIG. 5-4, anti-PS396 antibody did not respond to ppt fraction of HA-3R1N expressing cells and the ppt fraction of SH-SY5Y cells introduced the insoluble fraction from the Pick disease patient, while the antibody responded to the ppt fraction of HA-3R1N cells introduced the insoluble fraction from the Pick disease patient.

Figure 6:
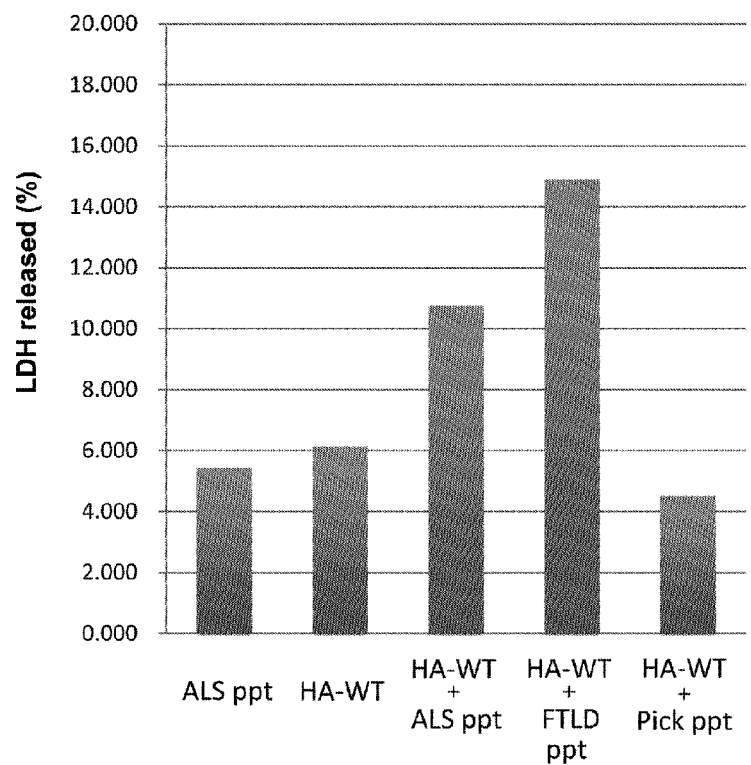
FIG. 6 is a graph showing results of cytotoxicity examination of cultured cells introduced insoluble fractions originated from patients of different diseases.

FIG. 6 is a graph showing results of cytotoxicity examination of cultured cells introduced the insoluble fractions originated from the patients of different diseases. The cytotoxicity ratio (%) was about 5% in the experiment group of untransfected SH-SY5Y cells into which the insoluble fraction originated from the ALS patient had introduced; about 6% in the experiment group of untransfected HA-TDP expressing cells into which the insoluble fraction from patient had not been introduced; and about 11%, about 15% and about 4.5% in the experiment group of HA-TDP expressing cells into which the insoluble fraction originated from ALS, FTLD and Pick's disease were introduced, respectively.

From the above results, it was shown that a specific combination of the accumulation of insoluble aggregates to become a nucleus (seed) of aggregation with the neurodegenerative-disease-related protein was needed in the accumulation of insoluble aggregates of various neurodegenerative diseases. And also, it was shown that the cell death was increased with the accumulation of insoluble aggregates. Furthermore, it was suggested that a cell culture model system with regard to the accumulation of insoluble aggregates can be constructed based on the insoluble fraction prepared from various neurodegenerative diseases and the neurodegenerative-disease-related proteins.

Example 3

1. Materials and Methods

The harvest of samples, preparation of insoluble fractions from the brain samples, preparation of sample for introduction including the insoluble fractions, cell culturing, preparation of transfectants, introduction of the insoluble fractions into the cultured cells and Western blotting were performed in accordance with the procedures similar to those in the example 1. After an introduction of insoluble fraction originated from the ALS patient into HA-TDP expressing cells, ppt fraction prepared from HA-TDP expressing cells (hereinafter referred to as "insoluble fraction for amplification" for ppt fraction) was introduced into new HA-TDP expressing cells.

2. Results

Figures 1, 7:
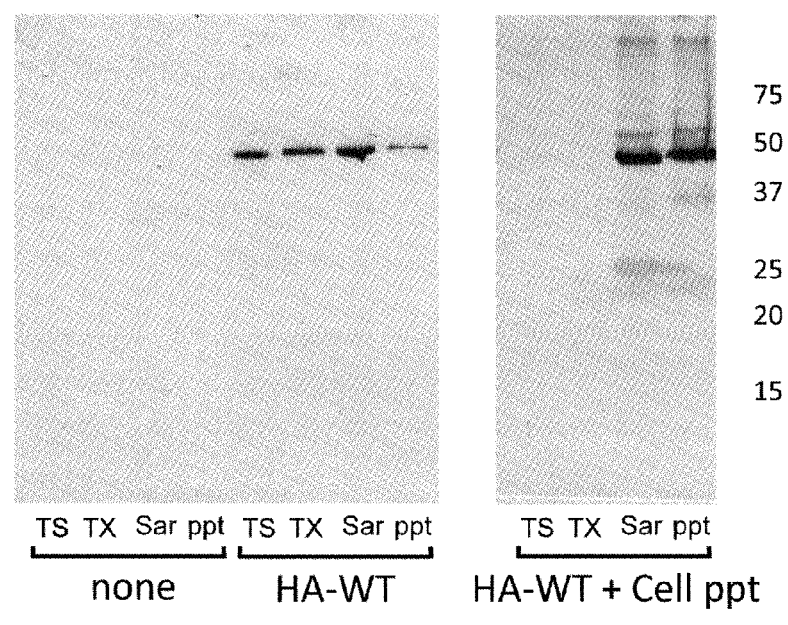
Figures 2, 7:
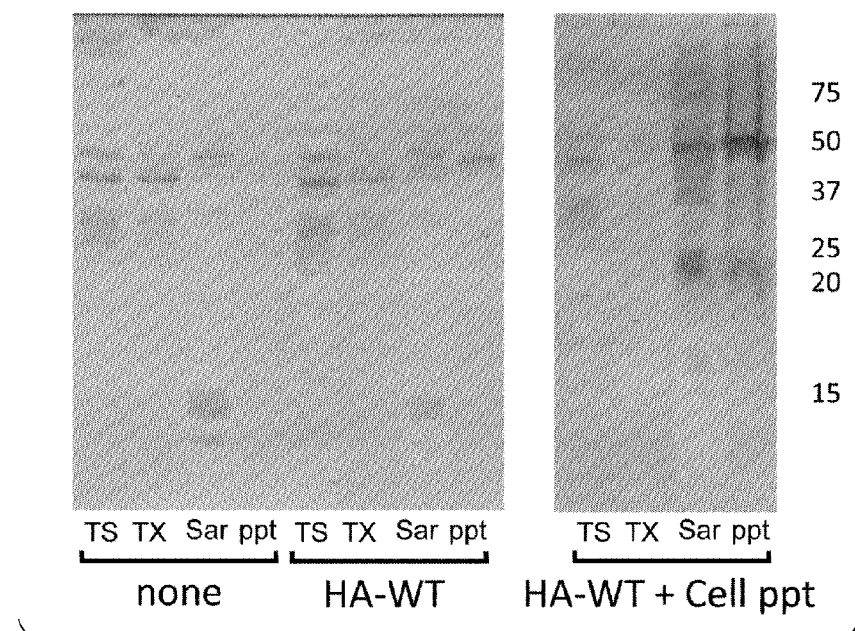

FIG. 7-1 is a Western blot image of HA-TDP expressing cells introduced an insoluble fraction for amplification and detected with anti-HA antibody. FIG. 7-2 is a Western blot image of HA-TDP expressing cells introduced an insoluble fraction for amplification and detected with anti-phosphorylated TDP antibody. The term "none" indicates a condition that an insoluble fraction from the brain of patient had not been introduced into the untransfected SH-SY5Y cells. A term "HA-WT" indicates a condition that the insoluble fraction from the brain of patient was not introduced into the HA-TDP expressing cells. The term "HA-WT+cell ppt" indicates a condition that the insoluble fraction for amplification was introduced into the HA-TDP expressing cells. Terms "TS", "TX", "Sar" and "ppt" indicate that TS, TX, Sar and ppt fractions of the cell treated under the condition of the "none", "WA-WT" or "HA-WT+cell ppt" were applied to each lane. As can be seen in FIGS. 7-1 and 7-2, anti-HA reacted strongly with the HA-TDP expressing cells introduced the insoluble fraction for amplification. And also, anti-409/410 antibody reacted with about 50 kDa intact TDP and about 25 kDa C-terminal fragment of TDP. From the above results, it was shown that the insoluble fraction from the cultured cells can form the insoluble aggregates, similar to the insoluble fraction from the neurodegenerative disease patient. Thus, when the insoluble fraction from the brain of neurodegenerative disease patient was introduced into the cultured cells expressed a monomer of neurodegenerative-disease-related protein, the insoluble fraction can become seeds and new insoluble aggregates were formed. In other words, the insoluble aggregates were amplified in the cultured cells. When the insoluble aggregates theseself were introduced into new cultured cells as seeds, the insoluble aggregates formed in the cultured cells can form the insoluble aggregates. Herewith, when the formation of the insoluble aggregates was repeated, the insoluble fraction originated from the brain of neurodegenerative disease patient was amplified on a large scale.

Certain band concentrations in blot images of FIGS. 1-3 and 7-2 were quantified with a densitometer, an amplification ratio of insoluble aggregates in the present invention was estimated based on measured value. When bands within a range from 20 kDa to 55 kDa at the ppt lane of the "HA-WT+ALS ppt" in FIG. 1-3 were measured with a densitometer, the measured value was 187,419,461 (A sarkosyl insoluble fraction was applied in the ppt lane wherein this fraction was obtained from the cell lysis of cells cultured for three days after introduction of sarkosyl insoluble fraction from the brain of ALS patient into HA-WT expressing cells.). This ppt fraction was suspended in 100 µL of PBS, and then 15 µL of samples were applied in Western blot images of FIG. 1-3 and 5 µL of samples were used in an introduction into new HA-WT expressing cells. Accordingly, the amounts of insoluble fraction before amplification were measured with a densitometer, its measured value was 62,473,153.65. When bands within a range from 20 kDa to 150 kDa at ppt lane of the "HA-WT+Cell ppt" in FIG. 7-2 were measured with a densitometer, its measured value was 278,226,669 (A sarkosyl insoluble fraction and an insoluble fraction amplified in the present invention was applied to the ppt lane.). The both of sar fraction and ppt fraction were suspended in PBS (100 µL), and then each sample (10 µL) were applied in Western blotting of FIG. 7-2. Accordingly, the amounts of insoluble fraction after amplification were measured with a densitometer, its measured value was 2,782,266,690. Then, a quotient (44.5 times) obtained by dividing 2,782,266,690 by 62,473,153.65 is estimated a value of amplification ratio of the insoluble aggregates. From the results, it was shown that a method of producing insoluble aggregates of neurodegenerative-disease-related protein in the present invention has at least a couple dozens times of amplification ratio.

Example 4

1. Material and Method

The harvest of samples, preparation of insoluble fractions from the brain samples, preparation of sample for introduction including the insoluble fractions, cell culturing, preparation of transfectants, introduction of the insoluble fractions into the cultured cells and Western blotting were performed in accordance with the procedures similar to those in the example 3. In this example, SH-SY5Y cells expressing intact non-HA-tagged TAR DNA binding protein (hereinafter referred to as "TDP" for intact non-HA-tagged TAR DNA binding protein) (hereinafter referred to as "TDP expressing cells" for SH-SY5Y cells expressing TDP) were also used. In three days after introduction of the insoluble fraction originated from the brain of ALS patient into the TDP expressing cells, the ppt fraction (hereinafter referred to as "insoluble fraction after the first amplification") of TDP expressing cells were recovered and used in Western blotting in conjunction with introduction into the TDP expressing cells. In three days after introduction of insoluble fraction after the first amplification, the ppt fraction (hereinafter referred to as "insoluble fraction after the second amplification") of the first HA-TDP expressing cells were recovered and used in Western blotting in conjunction with introduction into the second HA-TDP expressing cells. In three days after introduction of insoluble fraction after the second amplification, the ppt fraction (hereinafter referred to as "insoluble fraction after the second amplification") of the second HA-TDP expressing cells were recovered and used in Western blotting.

2. Results

Figure 8:
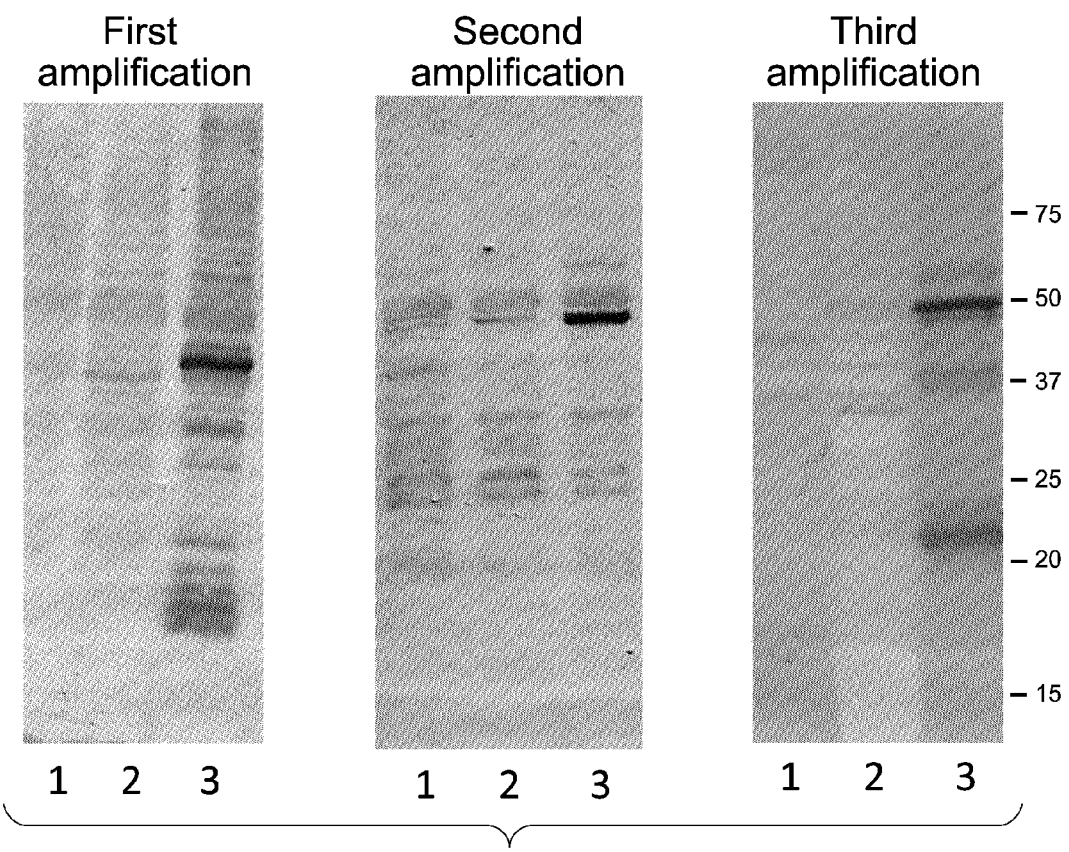
FIG. 8 is a Western blot image of insoluble fractions originated from TDP expressing cell after first, second or third amplifications from introduction of insoluble fraction originated from an ALS patient, and detected with anti-409/410 antibody.

FIG. 8 is a combination of Western blot images of insoluble fractions after the first, second or third amplifications detected with anti-409/410 antibody. Lane 1 in each of Western blot images was the ppt fraction of untransfected SH-SY5Y cells. Lane 2 in each of the Western blot images was HA-TDP expressing cells (the first round) or TDP expressing cells (the second and third rounds) which insoluble fraction had not been introduced. Lane 3 in each of Western blot images was insoluble fraction after the amplification of the first, second or third rounds. When lane 3 bands in the Western blot images of insoluble fraction after amplification of the first, second or third rounds were compared, the insoluble fraction after the first amplification was the fraction which non-tagged TDP had insolubilized an insoluble fraction from the brain of patient as a seeds, and thus a molecular weight was lower compared with the insoluble fractions after the second and third amplifications insolubilized a tagged TDP. When the amounts of the insoluble fraction after the first and third amplifications were quantified with a densitometer in accordance with the procedures similar to those in the example 3, the measured values were 1,534,573.82 and 52,345,813.5, respectively. Then, the amplification ratio of the two step amplifications of this example was a quotient (34.1 times) calculated by dividing 52,345,813.5 by 1,534,573.82.

Example 5

1. Materials and Methods

The harvest of samples, preparation of insoluble fractions from the brain samples, preparation of sample for introduction including the insoluble fractions, cell culturing, preparation of transfectants, introduction of insoluble fractions into the cultured cells and Western blotting were performed in accordance with the procedures similar to those in the example 3. In this example, the candidate compounds of therapeutic agent of neurodegenerative disease were added at final concentration of 20 µM at 6 hours after introduction of insoluble fraction originated from the brain of patient into HA-TDP expressing cells. As the candidate compounds; exifone (Tokyo Chemical Industry Co., Ltd., H1065), gossypetin (ChromaDex Inc. (Irvine, Calif.), ASB-00007390-010, Wako Pure Chemical Industries, Ltd.), myricetin (Sigma-Aldrich Japan Inc., M6760-10MG) and (−)-epicatechin gallate (Sigma-Aldrich Japan Inc., E3893-10MG) and as the control experiment; DMSO solvent were used. The candidate compounds were prepared to 20 mM solution using 100% DMSO as solvent, and added to cell culture media of HA-TDP expressing cells at 1/1000 dilution. Accordingly, DMSO was added at a final concentration of 0.1% in the control experiment. In three days after the introduction of insoluble fraction from the brain of patient, the ppt fraction of HA-TDP expressing cells was recovered and used in Western blotting, and the amounts of the insoluble fractions were quantified with a densitometer.

2. Results

Figure 9:
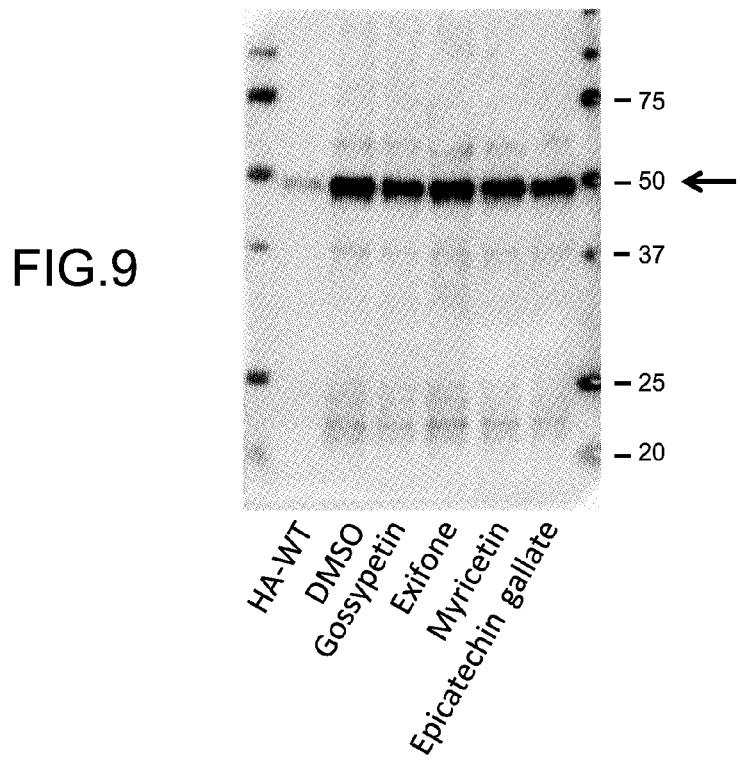
FIG. 9 is a Western blot image of insoluble fractions amplified in the presence of candidate compounds of therapeutic agent of neurodegenerative disease and detected with anti-409/410 antibody.
Figure 10:
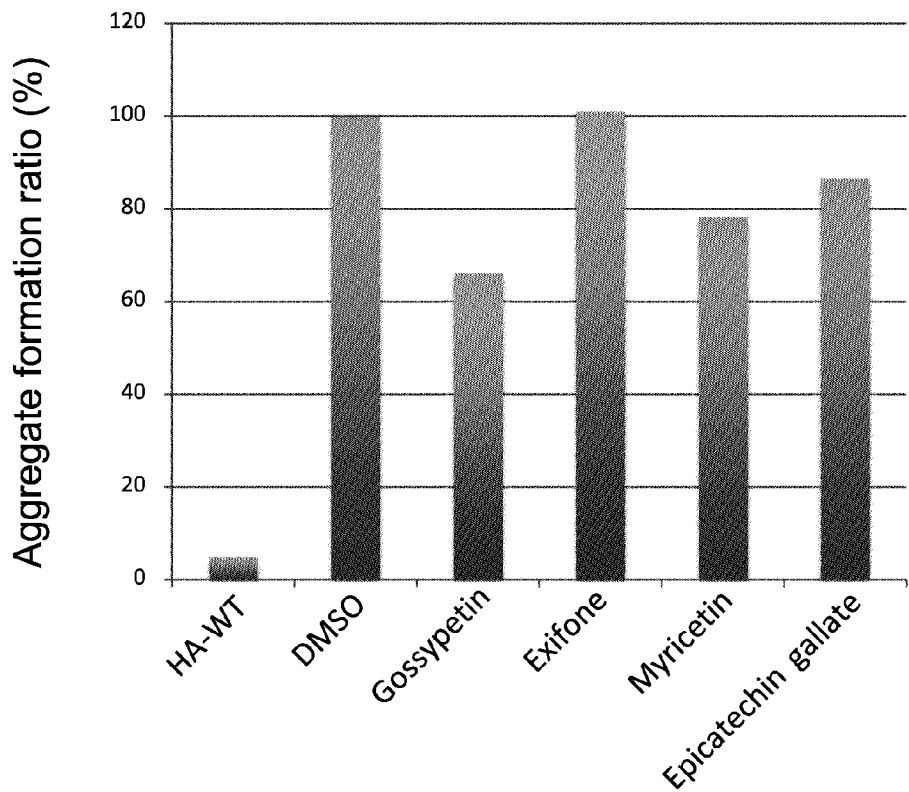
FIG. 10 is a column graph showing percentage of results quantified the insoluble aggregates at each lane in FIG. 9 with a densitometer, where the results are expressed by comparison with each control group of 100% amplified in the presence of the solvent DMSO.

FIG. 9 is a Western blot image of insoluble fractions amplified in the presence of candidate compounds of therapeutic agent of neurodegenerative disease and detected with anti-409/410 antibody. An arrow indicates a band of tagged TDP constituting insoluble aggregates. Each lane indicates HA-WT (condition; the fraction from the brain of patient had not been introduced into HA-TDP expressing cells.), DMSO (a solvent for candidate compounds of therapeutic agent for neurodegenerative disease), exifone, gossypetin, myricetin and epicatechin gallate, respectively. FIG. 10 is a column graph showing percentages of results quantified the insoluble aggregates at each lane in FIG. 9 with a densitometer, where the results were expressed by comparison with each control group as 100% amplified in the presence of the solvent DMSO. As can be seen in FIG. 10, with regard to therapeutic agent for neurodegenerative disease, the exifone did not have a suppressing effect against aggregate formation, while the epicatechin gallate, myricetin and gossypetin had the suppressing effect against aggregate formation. In the most effective gossypetin, approximately 40% of aggregate formation was suppressed. From the results, it was shown that a cell culture model system for the accumulation of insoluble aggregates of the present invention can be used to screen candidate compounds of therapeutic agent for neurodegenerative diseases.

INDUSTRIAL APPLICABILITY

As mentioned in the specification, a large amount of homogenous insoluble aggregates can be prepared according to the method of producing the insoluble aggregates of the present invention. Accordingly, the method of producing the insoluble aggregates of the present invention can provide the insoluble aggregates to a research institute which cannot obtain a biopsy sample comprising insoluble aggregates, and can develop a research on neurodegenerative diseases. Furthermore, the method for producing the insoluble aggregates of the present invention can provide a simple and inexpensive method of screening a therapeutic agent candidate for neurodegenerative disease.

What is claimed:

1. A method of amplifying in vitro a homogenous insoluble aggregate comprising TAR DNA-binding protein 43 kDa (TDP-43) protein and fragments thereof, comprising:
   (1) a step of introducing an insoluble aggregate originated from a brain of a neurodegenerative disease patient or from a biological sample of said patient into a cultured cell expressing a full-length TDP-43 protein in a constitutive manner;
   (2) a step of incubating the cultured cell with the insoluble aggregate already introduced thereinto, to obtain an amplified insoluble aggregate; and
   (3) a step of separating an amplified insoluble aggregate from the incubated cultured cell.

2. The method according to claim 1, further comprising (4) a step of amplifying a homogenous insoluble aggregate comprising TDP-43 protein and fragments thereof in a cultured cell, the step including:
   introducing the insoluble aggregate separated from the incubated cultured cell into the cultured cell expressing the full-length TDP-43 protein in the constitutive manner;

incubating the cultured cell with the insoluble aggregate already introduced thereinto, to obtain an amplified insoluble aggregate; and separating an amplified insoluble aggregate from the incubated cultured cell.

3. The method according to claim 2, further comprising (5) a step of further repeating the step of (4) in succession at least one time.

4. The method according to claim 3, wherein the cultured cell are expressing tagged full-length TDP-43 protein in a constitutive manner.

5. The method according to claim 4, wherein the tag is human influenza hemagglutinin (HA).

6. The method according to claim 2, wherein the cultured cell are expressing tagged full-length TDP-43 protein in a constitutive manner.

7. The method according to claim 6, wherein the tag is human influenza hemagglutinin (HA).

8. The method according to claim 1, wherein the cultured cell are expressing full-length TDP-43 protein linked to a tag in a constitutive manner.

9. The method according to claim 8, wherein the tag is human influenza hemagglutinin (HA).

* * * * *